United States Patent [19]

Akhavein et al.

[11] 4,366,777

[45] Jan. 4, 1983

[54] PEST CONTROLLING ANIMAL TAG

[75] Inventors: Ali A. Akhavein, Goldsboro; Gavin B. Braithwaite, Fremont, both of N.C.

[73] Assignee: ICI Americas Inc., Wilmington, Del.

[21] Appl. No.: 267,631

[22] Filed: May 27, 1981

[51] Int. Cl.³ ............................................ A01K 13/00
[52] U.S. Cl. ....................................... 119/156; 40/301
[58] Field of Search ................ 40/300, 301, 302, 303, 40/304; 119/106, 156; 424/28, 84; 128/114, 265

[56] References Cited

U.S. PATENT DOCUMENTS

| | | | |
|---|---|---|---|
| 2,911,756 | 11/1959 | Geary | 424/84 X |
| 4,059,074 | 11/1977 | Fürer et al. | 119/156 |
| 4,178,384 | 12/1979 | Ensing | 424/305 |
| 4,184,453 | 1/1980 | Ritchey | 40/301 X |

FOREIGN PATENT DOCUMENTS 104835  8/1980  Japan ................................ 119/156

OTHER PUBLICATIONS

F. W. Knapp and F. Herald, "Efficacy of Permethrin Ear Tags Against Face Flies and Horn Flies on Pastured Cattle," *Southwestern Entomologist*, Sep. 1980, pp. 183–186.

*Primary Examiner*—Robert P. Swiatek
*Attorney, Agent, or Firm*—John M. Sheehan; David J. Levy

[57] ABSTRACT

A pest controlling device for use with domestic or non-domestic animals comprising an identification tag which may contain indicia and a reservoir for gradual release of an active ingredient which surrounds and is held in place on the tag. A reservoir is further described which is adapted to be placed on various commercial animal tags.

30 Claims, 6 Drawing Figures

PEST CONTROLLING ANIMAL TAG

BACKGROUND OF THE INVENTION

The present invention relates to pest controlling active ingredient delivery systems for use with animals. In particular, a sustained release reservoir containing the active ingredient is provided for fast and reliable deployment on an animal identification tag.

Pest controlling agents may be used in association with animal identification tags or other devices attached directly or indirectly to the body of an animal such as a cow. For example, an ear tag for controlling the hog louse is described in U.S. Pat. No. 3,949,708. The tag of U.S. Pat. No. 3,949,708 has a spiked portion to insert through the ear of the animal, a pocket on a flat planar surface and an insecticide-impregnated pad to be inserted into the pocket. However, such tags have disadvantages since their use may require one to discard a non-insecticidal tag already on the animal and the closure means in the pocket to retain the pad may break which would require replacement again of the entire tag.

Other ear tags have insecticide impregnated throughout the body of the tag itself as described in "Tennessee Farm and Home Science", January - March 1978, Progress Report No. 105; in "The Southwestern Entomologist" Vol. 2, No. 1, March 1977 at pages 8-10; and in the "Journal of Economic Entomology" Vol. 63 (1970) pages 1688-1689; Vol. 70 (1977) pages 72-75, Vol. 71 (1978) pages 764-765, and Vol. 72 (1979) page 215. Again however, using such tags may require removing and discarding non-insecticidal tags already on the animal. Further, when impregnated tags lose effectiveness, a completely new tag must be inserted. Other active ingredient-containing devices for animals are described in U.S. Pat. Nos. 3,756,200 and 3,942,480.

SUMMARY OF THE INVENTION

An identifying and pest controlling device is provided which may be attached to an animal. The device comprises an identification tag and disposed about a portion of the tag such that it cannot fall off, a reservoir of a pest controlling active ingredient. Further, the reservoir for use as part of the device is an aspect of the present invention.

DETAILED DESCRIPTION OF THE INVENTION

Figure 1:
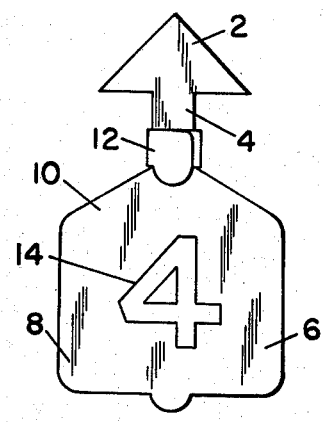
FIGS. 1 and 2 show the front and reverse sides, respectively, of an animal identification tag pest controlling device according to the invention.

The identification tags adapted to be attached to a portion of an animal may be virtually any animal identification tag used in the art. Examples include tags made of a polymer or metal with or without a pest controlling substance or other active ingredient contained in or on the tag. In general, such tags comprise three attached segments designated as 2, 4 and 6, respectively, in FIG. 1. The first segment 2 has a configuration to allow it to be readily inserted into and pulled through a portion of an animal to retain the tag on the animal. This first segment may have an arrowhead shape so that it can penetrate and exit the skin of an animal, e.g. the ear or the loose skin at the neck. The second tag segment 4 is a neck portion a part of which, after the tag has been inserted, remains within the animal. For the comfort of the animal and ease of application of the tag, the full neck portion will usually be longer than that which is actually necessary to be within the animal. It is at the tag neck portion which protrudes outside of the animal where the reservoir of the invention is most advantageously attached.

The third segment 6 of the animal tag is a relatively rigid and planar portion which may receive indicia or have indicia permanently attached. The third segment should have larger cross-sectional dimensions than the neck so that it cannot be readily pulled through the aperture in the skin of the animal. The third segment may have attached to it an insecticidal device as disclosed in U.S. Pat. No. 3,949,708, a ridge to facilitate placing the tag panel in a stencil wheel or other printing device as described in U.S. Pat. No. 3,357,122, a hole for placement of a colored button as provided in U.S. Pat. No. 3,512,289 or fringes which the animal could use to flick insects away as in U.S. Pat. No. 3,952,439.

Other animal identification tags to be inserted into the ear as well as tools for the insertion are disclosed in U.S. Pat. Nos. 3,334,434; 3,526,987; 3,552,051; 3,731,414; 3,867,777; 3,896,577; 3,916,904; 3,955,580; 3,979,847; 3,987,570; 4,000,744; and Reissue No. 29,536. Animal tags and tools for their insertion into the brisket, flank or neck skin of an animal are disclosed in U.S. Pat. No. 3,675,357 and 3,694,949. The pest controlling devices of the invention would normally be utilized with domestic animals such as cattle, sheep and pigs although they can be used with nondomesticated animals.

In addition to animal tags which are inserted into and through the skin of an animal, the reservoir of the invention may be affixed to identification tags which are attached to the animal by means such as a neck chain or leg band. Additionally, various identification tags are attached to the hair of animals by means of clamping or screwing devices.

The reservoir of the present invention is placed on the animal identification tag by encircling or surrounding a portion of the tag with it before or after the tag is attached to the animal. Thus, if desired the reservoir may be placed on the tag only when pests such as insects are a particular problem such as in the summer. Further, separate reservoirs with different pest controlling active ingredients may be used concurrently or consecutively depending on the particular target pest species to be controlled. This feature of the invention conveys advantages over tags impregnated with active ingredients since impregnated tags may be attached when pest control is not needed and one would not readily interchange tags if a different active ingredient is desirable, especially if for only a short period of time. Since the invention reservoir can be readily attached and detached without piercing the skin of the animal, one may be more likely to only use the active ingredient when necessary, thus minimizing animal contact with potentially hazardous pest controlling ingredients.

Figure 3:
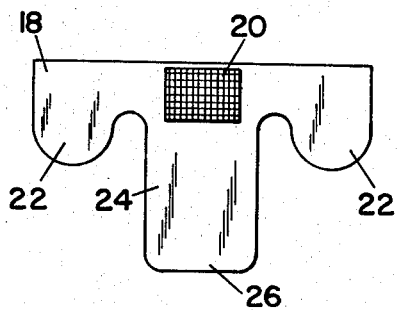
FIGS. 3 and 4 depict an active ingredient reservoir which may be used in the invention before and after, respectively, sealing the depository of the active ingredient. This depository was used in the device shown in FIGS. 1 and 2.
Figure 4:
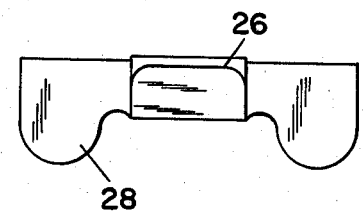

The reservoir may be any one of several designs. One arrangement is a thin, flexible tape or strip of a polymeric tape having a depository, e.g. an absorbent fibrous pad of felt or gauze, of the active ingredient attached. Preferably, the depository is smaller than the tape and is thus not completely coextensive with the tape portion. The tape is then bent around a relatively narrow portion of the tag and secured to itself, e.g. by a pressure sensitive adhesive which is then applied or which has been provided as a layer on the tape. Examples of this first arrangement are shown in FIGS. 3 and 4. The depository may be placed on either side of the tape although it is preferably placed on the side of the tape which is on the inside when the tape is attached to itself and surrounds a portion of the tag. Placing the depository on the inside allows it to be better protected and permits adjustment of active ingredient release by the number and size of the holes provided in the tape through which the active ingredient migrates. Of course, if the depository itself adjusts outward flow of the active ingredient, e.g. a cotton gauze soaked with active ingredient and coated with a light resinous film, the depository may be placed on the outside of the tape, i.e. the side of the tape not in contact with the tag. In this arrangement, the depository is essentially a wick of an absorbent material such as a natural fiber, e.g. cotton or wool, or a synthetic fiber or foam such as a polyurethane foam. Alternatively, a crushable ampoule within an absorbent fibrous sleeve may be the depository. When such a reservoir is to be deployed, it is attached to the tag and the ampoule of active ingredient is broken and the active ingredient soaks into the sleeve.

Although the reservoir could simply be directly secured only to the tag instead of to itself, this will often present problems since the tag may be coated with grease, oil, animal feed or other foreign substances. Thus, by having the reservoir surround a portion of the tag and secured to itself rather than solely to the tag, clear advantages are obtained. The tag need not be clean or even dry for the reservoir to be securely deployed.

Figure 5:
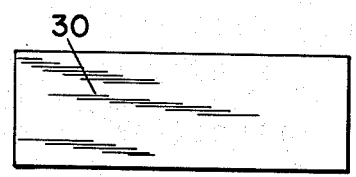
FIGS. 5 and 6 depict two types of active ingredient reservoir for use in the present invention.
Figure 6:
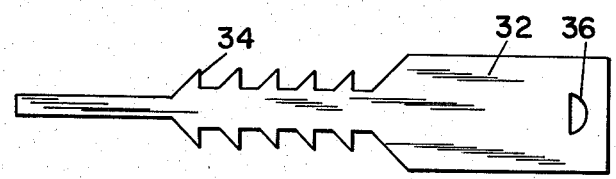

A second arrangement for the reservoir of the invention is a single- or multi-layered polymeric tape, such as shown in FIG. 5, in which an active ingredient is present in one or more solid polymeric layers and gradually migrates to one or both planar surfaces. The tape is bent around a portion of the tag and secured to itself by means such as adhesive, a staple, rivet or other fastener. Alternatively, the tape may be secured to itself without an adhesive or mechanical fastener by providing one end with spikes or flanges and the other with an aperture into which the spiked or flanged end may be inserted without being readily withdrawn, e.g. as shown in FIG. 6.

Materials and methods for their manufacture for the second arrangement of the reservoir of the invention are disclosed in U.S. Pat. Nos. 3,705,938; 3,857,934; 3,864,468; 4,102,991; and 4,160,335 which are hereby incorporated by reference. These patents describe methods of applying to a solid non-porous polymeric substrate sheeting a solid non-porous layer of a polymeric composition containing an active agent capable of migrating from the layer into and thoughout the substrate. The migrating active agent is incorporated in the layer in an amount sufficient to produce an effective level of activity on an exterior surface of the substrate. Polymeric strips containing a pest controlling agent homogenously dispersed throughout at least a portion of the polymeric matrix are available commercially as Vapona pest strips as described in U.S. Pat. No. 3,949,708; by a J. W. Gillett in Residue Review Vol. 44, pages 115 and 161 (1972); and in the Journal of Economic Entomology, Vol. 63, pages 1688–1689 (1970) and Vol. 69, pages 757–760 (1976).

The pest controlling active ingredient used in the present invention is one which kills, debilitates, repels, sterilizes, mutates or otherwise lessens the annoyance or harmful effects of any living organism associated with an animal. Examples of annoying or harmful living organisms include worms, fungi, bacteria, insects and other lower forms of life. In particular, the pests sought to be controlled by the invention are insects and more particularly flies such as the house fly, face fly, stable fly, horn fly, and ticks which may annoy or spread disease to cattle.

Particular pest controlling active ingredients are vapor-active insecticides or repellents or contact-effective insecticides such as the pyrethroids which include natural and synthetic materials such as pyrethrin, resmethrin, fenvalerate, cyhalothrin, decamethrin, bioresmethrin, permethrin and cypermethrin. Of particular effectiveness are the cyclopropanecarboxylate pyrethroids of the following formula

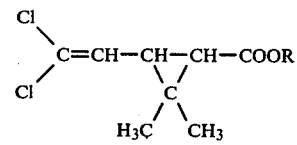

wherein R is 3-phenoxybenzyl for permethrin and R is α-cyano-3-phenoxy-benzyl for cypermethrin. These and other cyclopropanecarboxylate pyrethroids are described in U.S. Pat. Nos. 4,024,163 and 4,178,384. The active ingredient may be used neat, in a solvent or carrier, in the form of a dust or in combination with another active or inert ingredient, e.g. a dye, fragrance or anti-oxidant. Preferably, the active ingredient is a liquid, which includes a gum or semiliquid, and is used neat or highly concentrated to provide the greatest effect with the least inconvenience and weight.

Also part of the present invention is the method of controlling pests such as insects associated with an animal comprising deploying around an animal identification tag directly or indirectly attached to the animal, the pest controlling active ingredient reservoir as described.

FIG. 1 depicts a pest controlling device 8 according to the present invention. The device 8 comprises an animal identification tag 10 having a reservoir 12 of a pest controlling active ingredient surrounding a portion of the tag. The tag comprises a first or head segment 2 which has flanges, spikes, wings or other retaining members which are pliable and deformable to allow the insertion of the head segment into and through the skin of an animal. The second or neck portion 4 of the tag is narrower than both the head and body portions of the tag. The neck portion 4 is long enough to allow a part of it to remain within the skin of the animal, e.g. if the tag is an ear tag, the head portion 2 will protrude from the back of the ear and the body portion 6 from the front of the ear with the neck portion connecting the head and body portions and piercing through the ear. The third or body portion 6 of the tag is relatively rigid and flat with shoulders wider than the neck portion so that the tag remains on the animal after placement. The body portion may be blank for application of any desired indicia by the livestock manager althought the color or even the presence of a tag alone may provide suitable indicia or information for differentiation of the animal. The tag shown in FIG. 1 is provided with indicia 14 by printing, embossing or engraving. The reservoir 12 is an adhesive bandage provided with a gauze containing the active ingredient, as shown in FIGS. 3 and 4, and is affixed by being wrapped upon itself at the neck portion 4.

Figure 2:
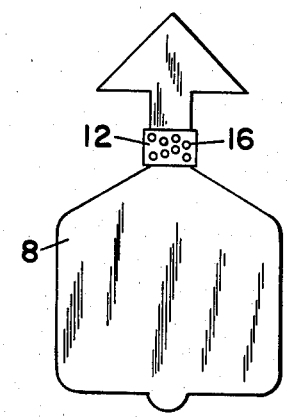

FIG. 2 is a view of the reverse side of the device 8 shown in FIG. 1. The reservoir 12 is provided with apertures 16 to allow the active agent to pass from the gauze through to the surface of the reservoir where it is then distributed over the animal. In the course of scratching and licking itself as well as coming into contact with other animals, minute but effective amounts of the active ingredient will rub off from the device and be deposited over the animal.

FIG. 3 depicts a unmounted reservoir 18 of the invention constructed of a thin sheet of flexible polymer 20 provided with a layer of a pressure sensitive adhesive onto which has been placed a depository 20 of the active ingredient, e.g. a cotton gauze soaked in an insecticide. The reservoir is provided with two end tabs 22 to affix the reservoir to itself around the animal tag and a center tab 24 which may be used to protect the depository 20 from moisture, sunlight or other elements which may degrade or dilute the active ingredient. After the active ingredient is in place in depository 20, the center tab 24 may be drawn up by its leading edge 26 and wrapped around the portion of the reservoir on which the depository is carried as shown in FIG. 4. The active ingredient will then migrate through the polymer sheet or through apertures punched in the reservoir to become gradually available on the reverse side of the reservoir shown in FIG. 3. The sustained release of the active ingredient may also be achieved by other means such as covering the depository 20 with a metal foil through which the active ingredient cannot migrate and allowing it to migrate through the polymer sheeting or holes punched therein. Alternatively, after the leading edge 26 has been drawn up and around the reservoir, the active ingredient can simply be allowed to seep out of the depository through the small fissures which will be present at the edges of the tape, e.g. at the joining of the center tab 24 to the reservoir. If the center tab 24 is not present or is shorter than that shown in FIG. 3, holes may be prepunched in the reservoir under the depository 20 to provide a pathway for the active ingredient. Thus, an example of a suitable reservoir for use in the invention is a Band-Aid adhesive bandage onto the gauze portion of which may be deposited an active ingredient.

FIG. 4 depicts the reservoir of FIG. 3 after being readied for deployment. Reservoir 28 of the invention can be secured to an animal tag as shown in FIGS. 1 and 2 after the leading edge 26 of the center tab, as shown in FIG. 3, has been drawn up and around the reservoir for protection of the depository. When the reservoir 28 is bent it may be secured by the pressure sensitive adhesive to itself by either bringing an adhesive surface of one end tab into contact with the non-adhesive back of the other end tab, the result being shown in FIG. 1, or the two adhesive faces of the end tabs may be adhered to each other. In the first case, the reservoir may also be adhered to the tag itself since only one adhesive face of an end tab will have been used to secure the reservoir to itself.

FIG. 5 depicts a laminated or single layer solid polymeric strip 30 which is impregnated with an active ingredient and which may be deployed as a reservoir surrounding a portion of an animal tag according to the invention. Such single- or multi-layered strips are set forth in U.S. Pat. No. 3,705,938 as described above.

FIG. 6 shows a self-tieing active ingredient reservoir 32 according to the invention. The reservoir 32 may be of a resilient polymeric material with active ingredient present in a depository which is smaller than the reservoir, as in the depository of FIG. 3, or it may be coextensive with the reservoir, as the reservoir of FIG. 5. In the latter, the active ingredient is homogenously dispersed throughout the polymeric matrix or is present in one or more layers of a laminate and migrates to the reservoir surface to give sustained release of the active ingredient. To deploy the reservoir of FIG. 6, it is bent around a neck portion of an animal tag and one or more of the barbed arrowhead-shaped protuberances 34 are inserted through the aperture 36 to encircle a portion of the animal tag. The shape and number of the arrowhead protuberances 34 may be varied considerably as long as the effect is to allow the reservoir to encircle the animal tag and be secured to itself in view of the fact that one or more parts of the reservoir are pulled through an aperture in the reservoir but cannot be easily pulled back out.

The reservoir of the invention, in addition to being deployed on an animal tag, may be used in association with poultry cages to combat pests such as the Northern fowl mite. In particular, one or more reservoirs may be placed on the bottom or side of a poultry cage and the random motions of the bird about the cage will insure some contact with the reservoir to effect control of the mites. The reservoir may be wrapped around two adjacent grid wires of the cage or it may be attached to a flat and narrow rigid strip of material which can be made of wood, metal, plastic or the like, e.g. a wooden tongue depressor or a large pair of tweezers. The strip with reservoir attached can then be readily inserted into the cage and withdrawn when desired, e.g. when the active ingredient has been depleted or its use is no longer required. When a large pair of tweezers is used, one reservoir can be attached to each tip and the tweezers can be inserted into two cages with the same motion, i.e. one tip into one cage and the other into the adjacent poultry cage, resulting in a significant advantage in time spent by the poultry manager.

What is claimed is:

1. A reservoir of a pest controlling active ingredient adapted to surround a part of an animal identification tag, said reservoir comprising:
   (a) a flexible tape portion having a pressure sensitive adhesive on one side thereof and attached to said tape portion,
   (b) a depository of an absorbent pad into which a liquid insecticide has been absorbed, said depository being not completely coextensive with the tape portion.

2. The reservoir of claim 1, wherein said insecticide is a contact-effective insecticide.

3. The reservoir of claim 2, wherein said insecticide is a cyclopropanecarboxylate pyrethroid.

4. The reservoir of claim 3, wherein said insecticide has the following formula:

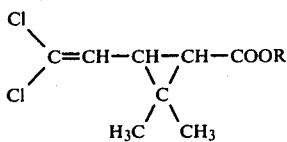

wherein R is 3-phenoxybenzyl or α-cyano-3-phenoxybenzyl.

5. The reservoir of claim 1, wherein said animal identification tag comprises a first segment which is adapted to penetrate and exit a portion of the animal to retain the tag on the animal.

6. The reservoir of claim 5, wherein said portion of the animal is an ear.

7. The reservoir of claim 5, wherein said animal identification tag comprises a further segment which is relatively rigid and planar and is adapted to receive indicia.

8. A pest controlling device for animals comprising: (i) an amnimal identification tag adapted to be attached to an animal, and (ii) a reservoir of a pest controlling active ingredient surrounding a portion of said tag, said reservoir comprising:
 (a) a flexible tape portion having a pressure sensitive adhesive on one side thereof and attached to said tape portion,
 (b) a depository of an absorbent pad into which a liquid insecticide has been absorbed, said depository being not completely coextensive with the tape portion.

9. The pest controlling device of claim 8, wherein said insecticide is a contact-effective insecticide.

10. The pest controlling device of claim 9, wherein said insecticide is a cyclopropanecarboxylate pyrethroid.

11. The pest controlling device of claim 10, wherein said insecticide has the following formula:

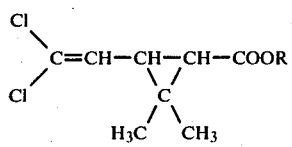

wherein R is 3-phenoxybenzyl or α-cyano-3-phenoxybenzyl.

12. The pest controlling device of claim 8, wherein said animaml identification tag (i) comprises a first segment which is adapted to penetrate and exit a portion of the animal to retain the tag on the animal.

13. The pest controlling device of claim 12, wherein said portion of the animal is an ear.

14. The pest controlling device of claim 12, wherein said animal identification tag (i) comprises a further segment which is relatively rigid and planar and is adapted to receive indicia.

15. A reservoir of a pest controlling active ingredient adapted to surround a part of an animal identification tag, said reservoir comprising:
 (a) a flexible tape portion having a pressure sensitive adhesive on one side thereof and attached to said tape portion,
 (b) a depository of an absorbent pad and a crushable ampoule containing a liquid insecticide, said depository being not completely coextensive with the tape portion.

16. The reservoir of claim 15, wherein said absorbent pad is a fibrous sleeve surrounding said crushable ampoule.

17. The reservoir of claim 15, wherein said insecticide is a contact-effective insecticide.

18. The reservoir of claim 17, wherein said insecticide is a cyclopropanecarboxylate pyrethroid.

19. The reservoir of claim 18, wherein said insecticide has the following formula:

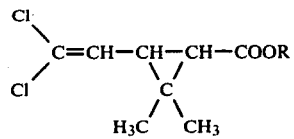

wherein R is 3-phenoxybenzyl or α-cyano-3-phenoxybenzyl.

20. The reservoir of claim 15, wherein said animal identification tag comprises a first segment which is adpated to penetrate and exit a portion of the animal to retain the tag on the animal.

21. The reservoir of claim 20, wherein said portion of the animal is an ear.

22. The reservoir of claim 20, wherein said animal identification tag comprises a further segment which is relatively rigid and planar and is adapted to receive indicia.

23. A pest controlling device for animals comprising: (i) an animal identification tag adapted to be attached to an animal, and (ii) a reservoir of a pest controlling active ingredient surrounding a portion of said tag, said reservoir comprising:
 (a) a flexible tape portion having a pressure sensitive adhesive on one side thereof and attached to said tape portion,
 (b) a depository of an absorbent pad and a crushable ampoule containing a liquid insecticide, said depository being not completely coextensive with the tape portion.

24. The pest controlling device of claim 23, wherein said absorbent pad is a fibrous sleeve surrounding said crushable ampoule.

25. The pest controlling device of claim 23, wherein said insecticide is a contact-effective insecticide.

26. The pest controlling device of claim 25, wherein said insecticide is a cyclopropanecarboxylate pyrethroid.

27. The pest controlling device of claim 26, wherein said insecticide has the following formula:

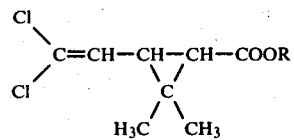

wherein R is 3-phenoxybenzyl or α-cyano-3-phenoxybenzyl.

28. The pest controlling device of claim 23, wherein said animal identification tag (i) comprises a first segment which is adapted to penetrate and exit a portion of the animal to retain the tag on the animal.

29. The pest controlling device of claim 28, wherein said portion of the animal is an ear.

30. The pest controlling device of claim 28, wherein said animal identification tag (i) comprises a further segment which is relatively rigid and planar and is adapted to receive indicia.

* * * * *